(12) United States Patent
Huang et al.

(10) Patent No.: US 11,975,146 B2
(45) Date of Patent: May 7, 2024

(54) POSITIONING SPUTUM SUCTION LARYNGEAL MASK

(71) Applicant: WUXI HOLY NOAH TECHNOLOGY CO., LTD, Wuxi (CN)

(72) Inventors: Dongxiao Huang, Wuxi (CN); Jun Zhou, Wuxi (CN); Hong Gao, Wuxi (CN); Tiegang Wei, Wuxi (CN); Jun Wang, Wuxi (CN); Zhentian Xiong, Wuxi (CN); Qian Wang, Wuxi (CN); Leibo Zhang, Wuxi (CN)

(73) Assignee: WUXI HOLY NOAH TECHNOLOGY CO., LTD, Wuxi (CN)

( * ) Notice: Subject to any disclaimer, the term of this patent is extended or adjusted under 35 U.S.C. 154(b) by 777 days.

(21) Appl. No.: 17/046,765

(22) PCT Filed: Apr. 19, 2019

(86) PCT No.: PCT/CN2019/083338
§ 371 (c)(1),
(2) Date: Oct. 9, 2020

(87) PCT Pub. No.: WO2019/223464
PCT Pub. Date: Nov. 28, 2019

(65) Prior Publication Data
US 2021/0121652 A1    Apr. 29, 2021

(30) Foreign Application Priority Data

May 24, 2018   (CN) .......................... 201810510775.1

(51) Int. Cl.
*A61M 16/04*      (2006.01)
*A61M 16/08*      (2006.01)

(52) U.S. Cl.
CPC .... *A61M 16/0488* (2013.01); *A61M 16/0463* (2013.01); *A61M 16/0816* (2013.01); *A61M 2210/1028* (2013.01)

(58) Field of Classification Search
CPC .......... A61M 16/0409; A61M 16/0463; A61M 16/0488; A61M 2210/1028
See application file for complete search history.

(56) References Cited

U.S. PATENT DOCUMENTS 5,241,956 A * 9/1993 Brain ................ A61M 16/0415
128/207.14
7,997,274 B2 * 8/2011 Baska ............... A61M 16/0415
128/207.14
(Continued)

FOREIGN PATENT DOCUMENTS

CN        101057994 A  * 10/2007   ............ A61M 16/04
CN        105498061 A  *  4/2016   ........ A61M 16/0463
(Continued)

*Primary Examiner* — Kathryn E Ditmer

(57) ABSTRACT

The invention relates to a positioning sputum suction laryngeal mask. The positioning sputum suction laryngeal mask comprises a mask body and a mask body tube, wherein the mask body comprises a mask body bottom plate and a mask main body arranged on the mask body bottom plate, a central region in the mask main body is provided with a mask body cavity communicated with the mask body tube, a stomach decompression tube corresponding to the stomach mouth is arranged on the back side of the mask body bottom plate, and the stomach decompression tube is isolated from the mask body cavity through the mask body bottom plate. The positioning sputum suction laryngeal mask also comprises a connection suction mechanism capable of realizing negative pressure suction in a gas supply process. The connection suction mechanism comprises a suction connecting tube which is arranged in the mask body bottom plate, and the end, located in the mask body bottom plate, of the (Continued)

suction connecting tube is communicated with the stomach decompression tube. The positioning sputum suction laryngeal mask can be effectively positioned, has lower complexity and usage costs, can ensure the ventilation and sealing effect without air inflation in use, can realize suction of secretions in a ventilation process, can avoid airway blockage caused by epiglottis, and can improve the stability and reliability in use.

11 Claims, 5 Drawing Sheets

(56) References Cited

U.S. PATENT DOCUMENTS

| | | | | |
|---|---|---|---|---|
| 10,314,995 B2* | 6/2019 | Sun | | A61B 1/267 |
| 10,549,056 B2* | 2/2020 | Wight | | A61M 16/0486 |
| 2003/0051734 A1* | 3/2003 | Brain | | A61M 16/0497 |
| | | | | 128/200.26 |
| 2005/0199244 A1* | 9/2005 | Tateo | | A61M 16/04 |
| | | | | 128/207.15 |
| 2008/0092903 A1* | 4/2008 | Nash | | A61M 16/0409 |
| | | | | 128/207.15 |
| 2008/0099026 A1* | 5/2008 | Chang | | A61M 16/0463 |
| | | | | 128/207.15 |
| 2008/0142017 A1* | 6/2008 | Brain | | A61M 16/0456 |
| | | | | 128/207.15 |
| 2009/0000622 A1* | 1/2009 | Murray | | A61M 16/0459 |
| | | | | 128/200.26 |
| 2010/0242957 A1* | 9/2010 | Fortuna | | A61M 16/04 |
| | | | | 128/207.15 |
| 2011/0023890 A1* | 2/2011 | Baska | | A61M 16/0415 |
| | | | | 128/207.14 |
| 2012/0174929 A1* | 7/2012 | Esnouf | | A61M 16/0409 |
| | | | | 128/207.15 |
| 2013/0269689 A1* | 10/2013 | Brain | | A61M 16/0057 |
| | | | | 128/202.16 |
| 2015/0114400 A1* | 4/2015 | Dubach | | A61M 16/04 |
| | | | | 128/207.15 |
| 2016/0136373 A1* | 5/2016 | Hansen | | A61M 16/0415 |
| | | | | 156/242 |
| 2016/0206841 A1* | 7/2016 | Vadivelu | | A61M 1/00 |
| 2020/0001032 A1* | 1/2020 | Zhou | | A61M 16/0447 |
| 2020/0261676 A1* | 8/2020 | Zhou | | A61M 16/209 |
| 2021/0162155 A1* | 6/2021 | Nasir | | A61M 16/0431 |

FOREIGN PATENT DOCUMENTS

| | | | |
|---|---|---|---|
| CN | 207871238 U * | 9/2018 | |
| DE | 202014005862 U1 * | 10/2014 | ............ A61M 16/04 |
| WO | WO-2014166136 A1 * | 10/2014 | ........ A61M 16/0409 |

* cited by examiner

POSITIONING SPUTUM SUCTION LARYNGEAL MASK

FIELD OF THE INVENTION

The invention relates to a laryngeal mask, in particular to a positioning sputum suction laryngeal mask, and belongs to the technical field of medical instruments.

BACKGROUND OF THE INVENTION

As a medical instrument for maintaining respiratory ventilation of patients, the laryngeal mask having the characteristic of a non-invasive airway has been widely applied to clinical anesthesia, emergency treatment or anabiosis. Along with the advances of materials and techniques, multiple improved laryngeal masks have been put to clinical use currently. However, the laryngeal masks in the prior art still have many problems.

Existing laryngeal masks adopt an airbag or a soft rubber ring to encircle the glottis to realize a sealing effect, such sealing is essentially to press the throat mucosa around the glottis by means of the airbag or the soft sealing ring, the pressure is vertical to a gas leakage pressure, the sealing effect is poor, and a bigger pressure is required to fulfill the clinical sealing effect, which usually results in postoperative throat pains; and gas leakage occurs usually when the pressure is low, which results in ventilation failure or mistaken aspiration caused by saliva flowing into the airway.

The existing laryngeal masks cannot realize effective sputum suction in a respiratory support period, and reluctant sputum suction usually results in gas leakage and frictional injuries to the throat. Airbag-type laryngeal masks which are widely used in clinic have high demands for the airbag pressure in use and require air inflation and deflation, thereby being tedious to use.

In respiratory support anesthesia, even tiny movement of the head or the neck of a patient may destroy a positioning relationship between the laryngeal mask and the glottis, which in turn may lead to reduction of the ventilation sealing performance of the laryngeal mask and even respiratory support failure. In order to realize respiratory support of the laryngeal mask, the position of the laryngeal mask with respect to the glottis generally needs to be adjusted again, and tracheal intubation is needed when the adjustment fails; and in this case, the difficulty in tracheal intubation will be increased greatly, troubles are brought to doctors, and risks are brought to patients.

In view of this, a better laryngeal mask, which can continuously and effectively suck and clear up excretions in oral cavity by means of a negative pressure in the respiratory support period, can avoid nasopharyngeal mucosa injuries caused by the continuous negative pressure and can also avoid frictional damage to a nasopharyngeal mucosa caused by the sputum suction tube, is needed clinically. As efficient sealing performance can be realized without air inflation and air deflation when the laryngeal mask is in use, the use success rate and safety of the laryngeal mask are improved; as enough sealing can be realized even if an extremely low pressure is applied to the mucosa part, postoperative throat pains of the patient are reduced; and as the laryngeal mask can be effectively positioned after being inserted, the positioning relationship between the laryngeal mask and the glottis will not be affected even the head or the neck moves.

BRIEF SUMMARY OF THE INVENTION

The present invention aims at providing a positioning sputum suction laryngeal mask to overcome the disadvantages in the prior art. The positioning sputum suction laryngeal mask has a compact structure, can be effectively positioned, has lower complexity and usage costs, can ensure the ventilation and sealing effect without air inflation in use, can realize the suction of secretions in a ventilation process, can avoid airway blockage caused by epiglottis, and can improve the stability and reliability in use.

According to the technical solution provided by the present invention, the positioning sputum suction laryngeal mask comprises a mask body capable of covering an oral mucosa around a glottis and a mask body tube adaptively connected to the mask body, wherein the mask body comprises a mask body bottom plate and a mask main body arranged on the mask body bottom plate, a central region in the mask main body is provided with a mask body cavity communicated with the mask body tube, and a stomach decompression tube corresponding to the esophagus opening is arranged on the back side of the mask body bottom plate and is isolated from the mask body cavity through the mask body bottom plate; and the positioning sputum suction laryngeal mask also comprises a connection suction mechanism capable of realizing negative pressure suction in a gas supply process, the connection suction mechanism comprises a suction connecting tube which is arranged in the mask body bottom plate, and the end, located in the mask body bottom plate, of the suction connecting tube is communicated with the stomach decompression tube.

The mask body tube is provided with a suction connector which is communicated with the suction connecting tube, and a bottom plate liquid guide port used for guiding oral secretions into the stomach decompression tube is arranged at the head end of the mask body bottom plate and is communicated with the stomach decompression tube.

Multiple hollow regions capable of guiding secretions at the nasopharyngeal part into the stomach decompression tube are arranged at the stomach decompression tube and are communicated with the stomach decompression tube.

A positioning body to be embedded into the esophagus is arranged at the head part of the mask body, and the length direction of the positioning body is consistent with that of the mask body bottom plate.

The positioning body is tubular or columnar.

At least one circle of sealing film is arranged on the upper part of the mask main body and is distributed on the outer circle of the mask main body and/or the inner circle in the mask body cavity in an encircling manner, and the joint of the mask main body and the glottis is sealed by the sealing film when the mask main body covers the glottis.

At least one circle of liquid guide film is arranged on the outer sidewall of the mask main body, the liquid guide film is matched with an adjacent liquid guide film or the sealing film arranged at the outer wall of the mask main body to form a liquid guide channel, and the liquid guide film is located between the mask body bottom plate and the sealing film.

A sealing film connector used for preventing the sealing film from turning up is arranged at the head end of the mask main body when the sealing film is distributed on the outer wall of the mask main body in the encircling manner, and the sealing film on the mask main body is connected with the sealing film connector.

A support bump is arranged at the bottom of the mask body cavity, and the support bump comprises a stomach decompression tube bump corresponding to the stomach decompression tube.

The mask body tube comprises a stomach decompression tube connecting pipe communicated with the stomach decompression tube and a mask body breather tube communicated with the mask body cavity, the stomach decompression tube connecting pipe and the mask body breather tube are isolated from each other, and an embedded positioning port communicated with the stomach decompression tube connecting pipe is arranged at the end, away from the mask body bottom plate, of the mask body tube.

The present invention has the following advantages: the suction connecting tube communicated with the stomach decompression tube is arranged in the mask body bottom plate, and after being connected with an external negative pressure suction device, the suction connecting tube can generate a negative pressure in the stomach decompression tube to realize a negative pressure purpose during gas supply; the sealing film is distributed on the outer circle of the mask body and/or the inner circle in the mask body cavity in the encircling manner, and the joint of the mask body and the glottis is sealed by the sealing film, so that the ventilation effect of the laryngeal mask is ensured without adopting an airbag for sealing, and the use success rate and safety of the laryngeal mask are improved; enough sealing can be realized even if an extremely low pressure is applied to the mucosa, so that postoperative throat pains of a patient are reduced, and the complexity and the using cost of the laryngeal mask can be reduced; the liquid guide film is arranged on the mask main body to guide liquid in the gas supply process; and as the positioning body which can be inserted into the esophagus is utilized, the laryngeal mask can be effectively positioned, the complexity and the using cost of the laryngeal mask can be reduced, airway blockage caused by the epiglottis can be avoided, and the stability and reliability in use can be improved.

Reference Signs: 1, mask body bottom plate; 2, stomach decompression tube; 3, mask body tube; 4, operating handle; 5, respirator connector; 6, positioning body; 7, positioning body liquid guide port; 8, sealing film connector; 9, liquid guide channel; 10, sealing film; 11, liquid guide film; 12, stomach decompression tube connecting pipe; 13, mask body breather tube; 14, suction connector; 15, hollow region; 16, stomach decompression tube port; 17, bottom plate liquid guide port; 18, embedded positioning port; 19, mask body cavity; 20, mask main body; 21, support bump; and 22, suction connecting tube.

DETAILED DESCRIPTION OF THE INVENTION

The present invention is further described below in combination with the accompanying drawings and embodiments.

Figure 1:
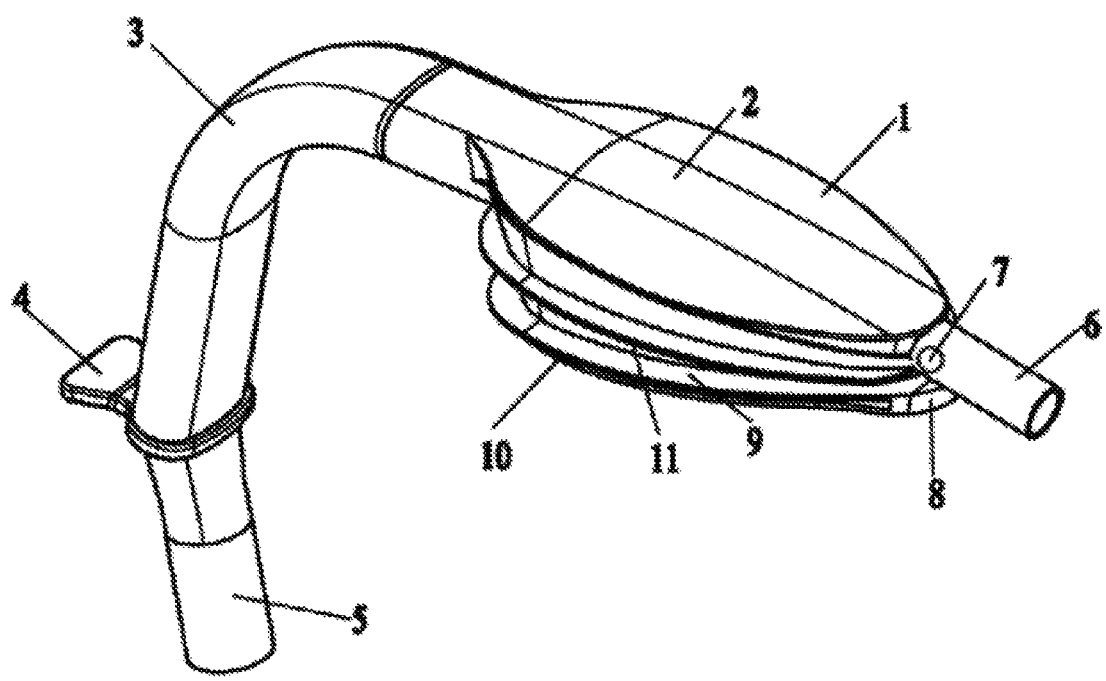
FIG. 1 is a perspective view when a positioning body is arranged on a mask body of the present invention.
Figure 2:
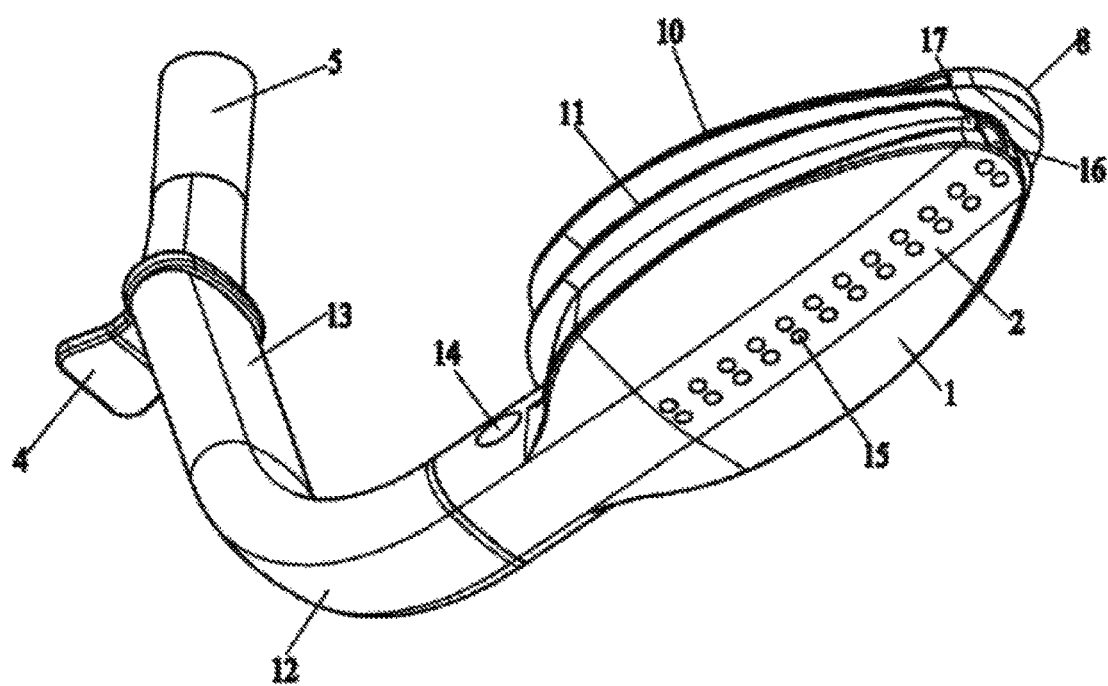
FIG. 2 is a perspective view when hollow regions are formed in a stomach decompression tube of the present invention.
Figure 3:
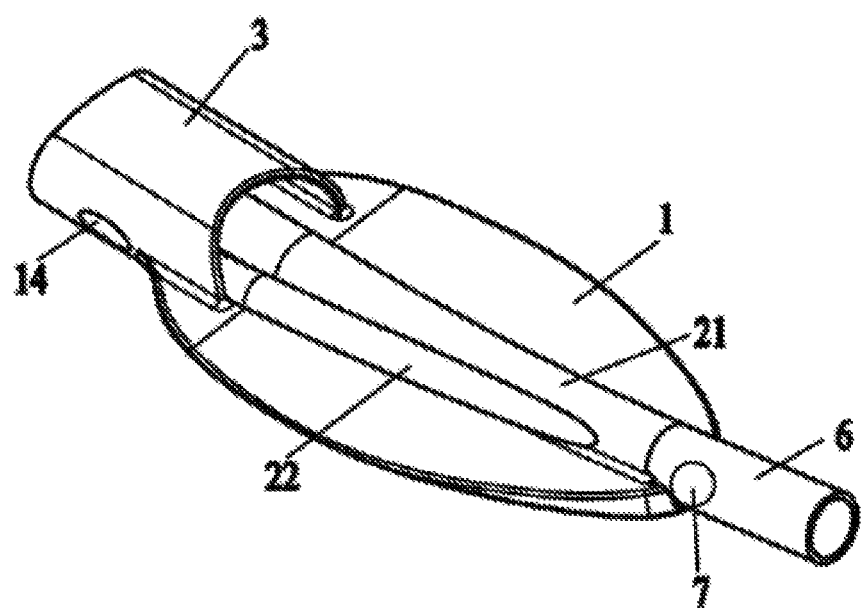
FIG. 3 is a schematic structural diagram of a mask body bottom plate of the present invention.
Figure 4:
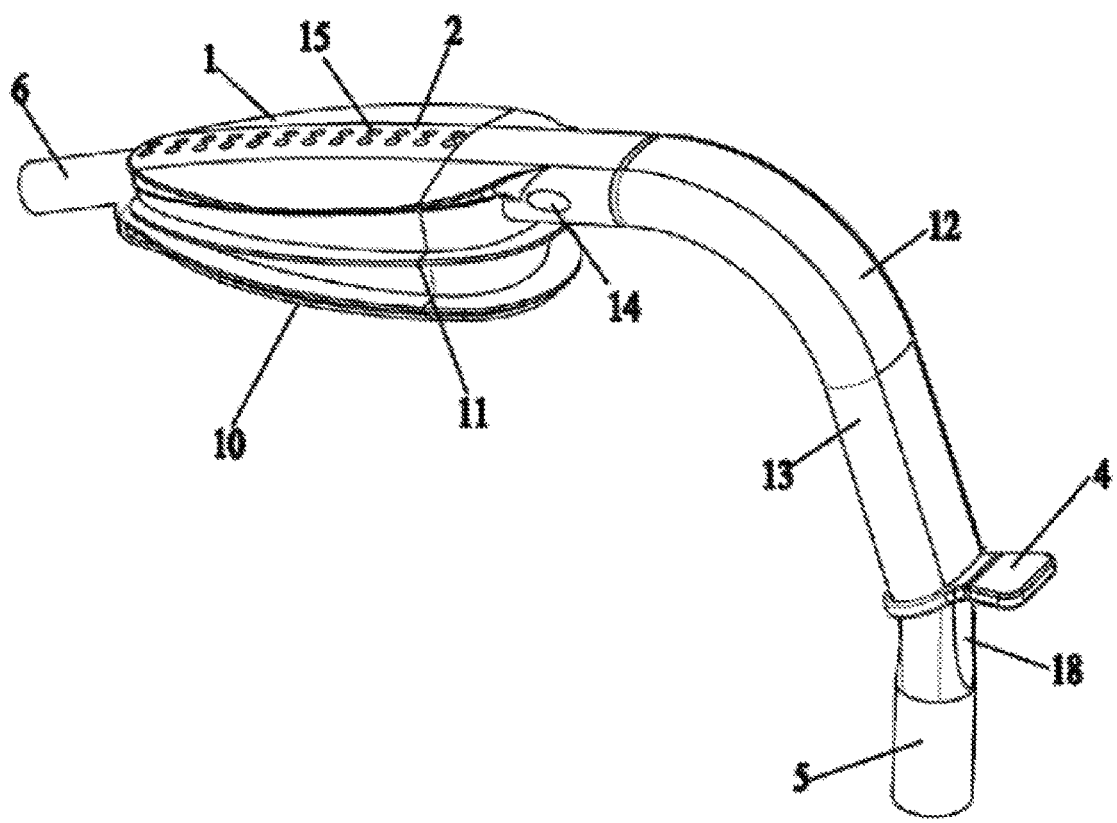
FIG. 4 is a perspective view of the positioning body and the hollow regions of the present invention.
Figure 5:
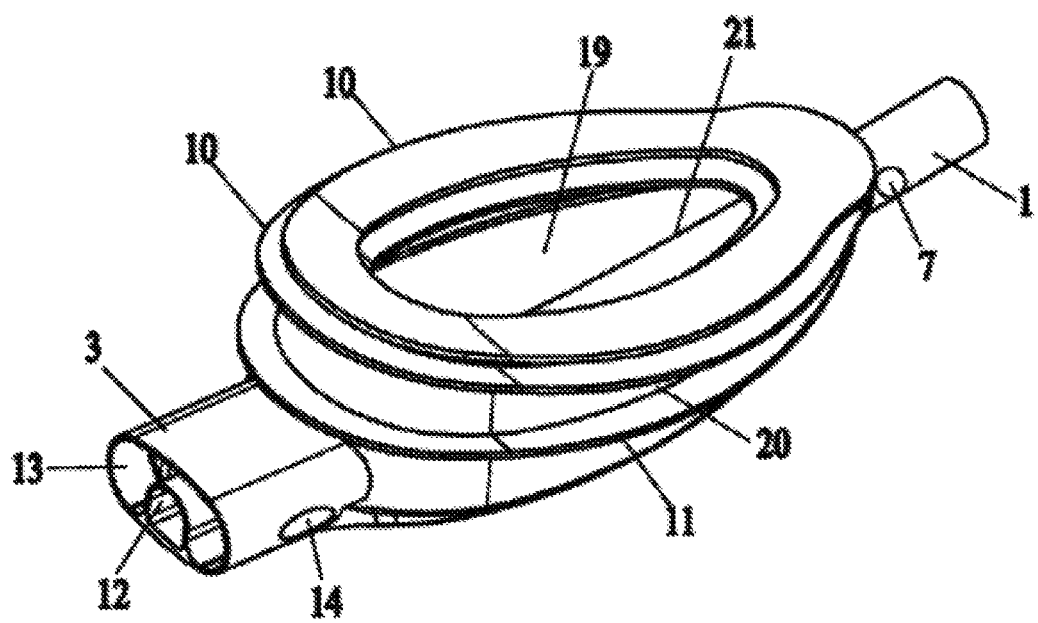
FIG. 5 is a t perspective view of the mask body of the present invention.

As shown in FIG. 1-FIG. 5, for the purpose of realizing excretion suction in a ventilation process of the laryngeal mask, the positioning sputum suction laryngeal mask comprises a mask body capable of covering an oral mucosa around the glottis and a mask body tube 3 adaptively connected to the mask body; the mask body comprises a mask body bottom plate 1 and a mask main body 20 arranged on the mask body bottom plate 1; a central region in the mask main body 20 is provided with a mask body cavity 19 communicated with the mask body tube 3, a stomach decompression tube 2 corresponding to the esophagus opening is arranged on the back side of the mask body bottom plate 1, and the stomach decompression tube 2 is isolated from the mask body cavity 19 through the mask body bottom plate 1; and The positioning sputum suction laryngeal mask also comprises a connection suction mechanism capable of realizing negative pressure suction in a gas supply process; the connection suction mechanism comprises a suction connecting tube 22 which is arranged in the mask body bottom plate 1; and the end, located in the mask body bottom plate 1, of the suction connecting tube 22 is communicated with the stomach decompression tube 2.

To be specific, the mask body and the mask body tube 3 are made of materials which are in accordance with the medical standard; the mask body covers the glottis in use, that is to say, the mask body covers the oral mucosa around the glottis in an encircling manner; generally, the end, connected with the mask body tube 3, of the mask body is a tail end of the mask body while the other end of the mask body serves as a head end of the mask body; the shape formed by cooperation of the mask body and the mask body tube 3 is same as that of existing laryngeal masks, that is, the mask body is heart-shaped or oblong; the region, near the mask body, of the mask body tube 3 is bent, and the mask body tube 3 can be bent to realize operations such as gas supply and insertion.

In this embodiment, the mask body bottom plate 1 and the mask main body 20 form the structure of the mask body, the mask main body 20 is arranged on the mask body bottom plate 1, and the mask main body 20 covers the oral mucosa around the glottis in an encircling manner. Generally, the mask body bottom plate 1 and the mask main body 20 are integrally formed, and the thickness of the mask main body 20 is greater than that of the mask body bottom plate 1; and the mask main body 20 and the mask body bottom plate 1 are made of soft materials such as medical silica gel to avoid injuries to the airway, the glottis and the like in use. In order to meet the demand for gas supply, the mask body cavity 19 is arranged in the mask main body 20 and is located in the central region of the mask main body 20, the mask body tube 3 is communicated with the mask body cavity 19 and the mask body cavity 19 can be connected with a respirator and the like through the mask body tube 3, and after covering the glottis, the mask main body 20 is connected with the mask body cavity 19 in a matching manner through the mask body tube 3 to form a gas supply channel.

The stomach decompression tube 2 is arranged at the back side of the mask body bottom plate 1, the axis of the stomach decompression tube 2 is basically overlapped with the axis of the mask body bottom plate 1, the stomach decompression tube 2 is as long as the mask body bottom plate 1, and a stomach decompression tube port 16 of the stomach decompression tube 2 is located at the head end of the mask body bottom plate 1 and corresponds to the esophagus opening when the mask main body covers the oral mucosa around the glottis, so that gastric juice or gas in the stomach can be guided out through the stomach decompression tube 2.

In the gas supply process of the laryngeal mask, the connection suction mechanism is arranged to realize negative pressure suction; the connection suction mechanism can suck out excretions in the oral cavity in the gas supply process. To be specific, the suction connecting tube 22 of the connection suction mechanism is arranged in the mask body bottom plate 1; the end, close to the head end of the mask body bottom plate 1, of the suction connecting tube 22 is communicated with the stomach decompression tube 2; the end, away from the mask body bottom plate 1, of the suction connecting tube 22 can be connected with the negative pressure suction device; after being connected with the negative pressure suction device, the suction connecting tube 22 forms a negative pressure in the stomach decompression tube 2 through the suction connecting tube 22; and after the negative pressure is formed in the stomach decompression tube 2, gas, gastric juice or oral secretions in the stomach enter the stomach decompression tube 2 and are sucked out.

During specific implementation, a suction connecting catheter is fixedly arranged at the end, away from the mask body bottom plate 1, of the suction connecting tube 22; the suction connecting tube 22 is connected with an external negative pressure suction device through the suction connecting catheter; the suction connecting catheter is detachably connected with the negative pressure suction device; the negative pressure suction device can be of an existing common structure as specifically needed and will not be detailed anymore herein. In addition, the suction connecting tube 22 is obliquely distributed on the mask body bottom plate 1, and the suction connecting tube 22 and the mask body cavity 19 are disconnected with each other.

Furthermore, a suction connector 14 communicated with the suction connecting tube 22 is arranged on the mask body tube 3, and a bottom plate liquid guide port 17 used for guiding oral secretions into the stomach decompression tube 2 is also arranged at the head end of the mask body bottom plate 1 and is communicated with the stomach decompression tube 2.

In this embodiment, the suction connector 14 is arranged on the mask body tube 3 and can be located at the end, away from the mask body bottom plate 1, of the suction connecting tube 22. The bottom plate liquid guide port 17 is located at the head end of the mask body bottom plate 1 and is communicated with the stomach decompression tube 2; oral secretions on the mask body bottom plate 1 can flow into the stomach decompression tube 2 via the bottom plate liquid guide port 17 so as to be subsequently sucked by means of a negative pressure; and the oral secretions include saliva and the like.

Furthermore, multiple hollow regions 15 capable of guiding secretions of the nasopharyngeal part into the stomach decompression tube 2 are arranged on the stomach decompression tube 2 and are communicated with the stomach decompression tube 2. In this embodiment, the hollow regions 15 run through the stomach decompression tube 2 and are hole-shaped or groove-shaped; when the hollow regions 15 are hole-shaped, the multiple hollow regions 15 are uniformly distributed on the stomach decompression tube 2 in the lengthwise direction of the stomach decompression tube 2; and when the hollow regions 15 are groove-shaped, the groove-shaped hollow regions 15 are distributed in the lengthwise direction of the stomach decompression tube 2, or the length of the hollow regions 15 is smaller than that of the stomach decompression tube 2. Secretions of the nasopharyngeal part can enter the stomach decompression tube 2 through the hollow regions 15, so that suction of the secretions of the nasopharyngeal part is realized. In addition, when the hollow regions 15 on the stomach decompression tube 2 are groove-shaped, the stomach decompression tube can be positioned by the hollow regions 15, that is, the stomach decompression tube can be embedded in the groove-shaped hollow regions 15; and when the stomach decompression tube is embedded in the hollow regions 15, the influence of the stomach decompression tube on the sealing performance of the laryngeal mask during ventilation also can be avoided.

During specific implementation, the mask body tube 3 comprises a stomach decompression tube connecting pipe 12 communicated with the stomach decompression tube 2 and a mask body breather tube 13 communicated with the mask body cavity 19; the stomach decompression tube connecting pipe 12 and the mask body breather tube 13 are isolated from each other; and an embedded positioning port 18 communicated with the stomach decompression tube connecting pipe 2 is arranged at the end, away from the mask body bottom plate 1, of the mask body tube 3.

In this embodiment, the stomach decompression tube connecting pipe 12 is correspondingly communicated with the stomach decompression tube 2, the mask body breather tube 13 is communicated with the mask body cavity 19, a respirator connector 5 is arranged at the end of the mask body breather tube 13, the mask body breather tube 13 can be connected with the external respirator through the respirator connector 5, the respirator forms a gas supply channel through the mask body cavity 19 after the mask body breather tube 13 is connected with the external respirator, and the stomach decompression tube connecting pipe 12 and the mask body breather tube 13 are disconnected. The embedded positioning port 18 is only communicated with the stomach decompression tube connecting pipe 12, that is, the embedded positioning port 18 and the mask body breather tube 13 are in a disconnected state. In addition, the mask body tube 3 is also provided with an operating handle 4, and the embedded positioning port 18 is located at the outer side of the operating handle 4.

During specific implementation, the negative pressure suction state in the stomach decompression tube 2 can be adjusted by means of the connecting state in the embedded positioning port 18 and the stomach decompression tube 2; when the embedded positioning port 18 is in an open state, external gas can enter the stomach decompression tube 2 via the embedded positioning port 18 to prevent an excessively-high negative pressure of the negative pressure suction device, which may otherwise result in injuries to the oral mucosa during negative pressure suction; when the negative pressure suction effect needs to be improved, the embedded positioning port 18 can be closed to prevent external gas from entering the stomach decompression tube 2 at the moment; the negative pressure state in the stomach decompression tube 2 also can be correspondingly adjusted when the embedded positioning port 18 is in an half-opened state, so that pressure adjustment in the suction process can be realized while the adaptability of the negative pressure suction device is ensured.

Furthermore, a positioning body 6 capable of being embedding into the esophagus is also arranged at the head end of the mask body, and the length direction of the positioning body 6 is consistent with the length direction of the mask body bottom plate 1. In this embodiment, the positioning body 6 is arranged at the head of the mask body bottom plate 1, and is installed on the mask main body 20. The outer diameter of the positioning body 6 is far smaller than the width of the mask body bottom plate 1, the positioning body 6 can be embedded into the esophagus, and after the positioning body 6 is embedded into the esophagus, the laryngeal mask can be positioned to be prevented against deviation, which may otherwise affect the ventilation effect.

During specific implementation, the positioning body 6 is tubular or columnar. When the positioning body 6 is tubular, the positioning body 6 is communicated with the stomach decompression tube 2 and corresponds to the stomach decompression tube port 16, and in this case, a gastroscope can be embedded into the stomach through the stomach decompression tube 2 and the positioning body 6, so that the gastroscope embedding requirement is met while the laryngeal mask is positioned. When the gastroscope is embedded, the gastroscope stretches in from the embedded positioning port 18, sequentially penetrates through the stomach decompression tube connecting pipe 12, the stomach decompression tube 2 and the positioning body 6, and finally stretches out of the positioning body 6. In addition, a positioning body liquid guide port 7 is arranged on the positioning body 6, oral secretions such as saliva can enter the stomach decompression tube 2 via the positioning body liquid guide port 7 and the positioning body liquid guide port 7 is close to the joint of the positioning body 6 and the mask body bottom plate 1. When the positioning body 6 is of a columnar structure, the positioning body 6 will not block the stomach decompression tube port 16, that is, the positioning body 6 will not affect the negative pressure suction effect. In addition, the positioning body 6 can also be in other shapes such as an open tubular shape, and the specific shape of the positioning body 6 can be selected as needed, and unnecessary details will not be given anymore herein.

Furthermore, at least one circle of sealing film is arranged at the upper part of the mask main body 20, the sealing film is distributed at the outer circle of the mask main body 20 and/or the inner circle in the mask body cavity 19 in an encircling manner, and the joint of the mask main body 20 and the glottis is sealed by the sealing film when the mask main body 20 covers the glottis.

In order to guarantee the gas supply state, at least one circle of sealing film is arranged at the upper part of the mask main body 20, and the sealing film is distributed at the outer circle of the mask main body 20 and/or the inner circle in the mask body cavity 19 in an encircling manner; and the joint of the mask main body 20 and the glottis is sealed by the sealing film when the mask main body 20 covers the glottis, so that the ventilation effect is ensured. That is, the sealing film is arranged on the outer wall of the mask body and is uniformly distributed along the outer wall of the mask main body 20; or the sealing film is arranged in the mask body cavity 19 and is consistent with the mask body cavity 19 in shape, and the sealing film in the mask body cavity 19 will not affect the normal ventilation state of the mask body cavity 19. Clearly, sealing films can also be arranged both on the outer wall of the mask main body 20 and in the mask body cavity 19, and the distribution of the sealing film on the mask main body 20 can be selected as needed.

Compared with the existing laryngeal masks, an airbag or other similar structures do not need to be arranged the mask body. During ventilation, the mask body cavity 19 is in a positive pressure state, and the air pressure formed during gas supply enables the sealing film to be tightly attached to the joint of the mask main body 20 and the glottis, that is, the sealing film can seal the mucosa around the glottis, and the use success rate and safety of the laryngeal mask are improved without air inflation and air deflation; and as enough sealing can be realized even if an extremely low pressure is applied to the mucosa, postoperative throat pains of a patient are reduced.

The sealing film can be made of a thin film and is matched with the mask main body 20 to effectively reduce complexity and production and using costs of the laryngeal mask. During specific implementation, the edge of the sealing film warps up in the direction away from the mask body bottom plate 1, and the sealing effect of the sealing film on the joint of the mask body 20 and the glottis is further improved during gas supply after the edge of the sealing film turns up.

Furthermore, at least one circle of liquid guide film 11 is arranged at the outer sidewall of the mask main body 20, the liquid guide film 11 is matched with an adjacent liquid guide film 11 or the sealing film on the outer wall of the mask main body 20 to form a liquid guide channel 9; and the liquid guide film 11 is located between the mask body bottom plate 1 and the sealing film.

In this embodiment, the liquid guide film 11 is located in the central region of the mask main body 20, the liquid guide film 11 also encircles the outer circle of the mask main body 20, and the liquid guide film 11 and the sealing film are distributed in parallel. In the accompanying drawings, two circles of sealing films are arranged on the mask main body 20, a gap is reserved between the two circles of sealing films, and a gap reserved between the sealing film and the liquid guide film 11 forms a the channel 9 for guiding saliva; of course, the channel 9 for guiding saliva also can be formed by the gap between the two circles of sealing films; that is, saliva can flow towards the head end of the mask body via the corresponding liquid guide channel 9 and can accordingly enter the stomach decompression tube 2 via the bottom plate liquid guide port 17 or the positioning body liquid guide port 7 during gas supply.

Furthermore, a sealing film connector 8 used for preventing the sealing film from turning up is arranged at the head end of the mask main body 20 when the sealing film is distributed at the outer wall of the mask main body 20 in the encircling manner, and the sealing film on the mask main body 20 is connected with the sealing film connector 8.

In this embodiment, the sealing film connector 8 is located at the head end of the mask main body 20, the shape of the sealing film connector 8 is adaptive to the shape of the head end of the mask body 20, the sealing films on the mask main body 20 can be connected through the sealing film connector 8, the sealing film connector 8 is made of hard materials; the sealing film connector 8 can prevent the sealing film from turning up when the mask main body 20 is embedded, so that the sealing effect of the sealing film on the joint of the mask main body 20 and the glottis will not be affected. The sealing film connector 8 is located above the stomach decompression tube port 16 of the stomach decompression tube 2 and thus will not affect normal use of the stomach decompression tube 2.

Furthermore, a support bump 21 comprising a stomach decompression tube bump corresponding to the stomach decompression tube 2 is arranged at the bottom of the mask body cavity 19.

In this embodiment, the support bump 21 is located in the mask body cavity 19 and corresponds to the stomach decompression tube 2, the support bump 21 is arc-shaped in the mask body cavity 19, and the support bump 21 in the mask body cavity 19 protrudes out of the mask body bottom plate 1 to form the stomach decompression tube bump; certainly, the support bump 21 and the stomach decompression tube 2 can also be in a non-corresponding state. In addition, the support bump 21 may also comprise a suction connecting tube bump corresponding to the suction connecting tube 22, and the height of the suction connecting tube bump may be smaller than that of the stomach decompression tube bump.

When the mask main body 20 covers the glottis, the support bump 21 is matched with the epiglottis to prevent the epiglottis from blocking communication between the mask body breather tube 13 in the mask body tube 3 and the mask body cavity 19, that is, the gas channel will not be blocked, thus ensuring ventilation stability and reliability.

What is claimed is:

1. A positioning sputum suction laryngeal mask, comprising a mask body capable of covering an oral mucosa around a glottis and a mask body tube (3) connected to the mask body, wherein the mask body comprises a mask body bottom plate (1) and a mask main body (20) arranged on the mask body bottom plate (1), a central region in the mask main body (20) is provided with a mask body cavity (19) communicated with the mask body tube (3), and a stomach decompression tube (2) corresponding to a esophagus opening is arranged on a back side of the mask body bottom plate (1) and is isolated from the mask body cavity (19) through the mask body bottom plate (1);

and the positioning sputum suction laryngeal mask also comprises a connection suction mechanism capable of realizing negative pressure suction in a gas supply process, the connection suction mechanism comprises a suction connecting tube (22) which is arranged in the mask body bottom plate (1), and an end, located in the mask body bottom plate (1), of the suction connecting tube (22) is communicated with the stomach decompression tube (2);

wherein multiple hollow regions (15) capable of guiding secretions at a nasopharyngeal part into the stomach decompression tube (2) are arranged on the stomach decompression tube (2) and are communicated with the stomach decompression tube (2).

2. The positioning sputum suction laryngeal mask according to claim 1, wherein the mask body tube (3) is provided with a suction connector (14) which is communicated with the suction connecting tube (22), and a bottom plate liquid guide port (17) for guiding oral secretions into the stomach decompression tube (2) is arranged at a head end of the mask body bottom plate (1) and is communicated with the stomach decompression tube (2).

3. The positioning sputum suction laryngeal mask according to claim 2, wherein a positioning body (6) to be inserted into an esophagus is arranged on a head of the mask body, and a length direction of the positioning body (6) is aligned with that of the mask body bottom plate (1).

4. The positioning sputum suction laryngeal mask according to claim 3, wherein the positioning body (6) is tubular or columnar.

5. The positioning sputum suction laryngeal mask according to claim 1, wherein a positioning body (6) to be inserted into an esophagus is arranged on a head of the mask body, and a length direction of the positioning body (6) is aligned with that of the mask body bottom plate (1).

6. The positioning sputum suction laryngeal mask according to claim 5, wherein the positioning body (6) is tubular or columnar.

7. The positioning sputum suction laryngeal mask according to claim 1, wherein at least one sealing film (10) is arranged on an upper part of the mask main body (20) and is distributed at an outer circle of the mask main body (20) and/or an inner circle in the mask body cavity (19) in an encircling manner, and a joint of the mask main body (20) and the glottis is sealed by the at least one sealing film (10) when the mask main body (20) covers the glottis.

8. The positioning sputum suction laryngeal mask according to claim 7, wherein at least one circle of liquid guide film (11) is arranged on an outer sidewall of the mask main body (20) and is matched with an adjacent liquid guide film (11) or the at least one sealing film (10) to form a liquid guide channel, and the at least one circle of liquid guide film (11) is located between the mask body bottom plate (1) and the at least one sealing film (10).

9. The positioning sputum suction laryngeal mask according to claim 7, further comprises a sealing film connector (8) connected to the at least one sealing film (10) for preventing the at least one sealing film (10) from turning up.

10. The positioning sputum suction laryngeal mask according to claim 1, wherein a support bump (21) is arranged at a bottom of the mask body cavity (19), and the support bump (19) comprises a stomach decompression tube bump corresponding to the stomach decompression tube (2).

11. The positioning sputum suction laryngeal mask according to claim 1, wherein the mask body tube (3) comprises a stomach decompression tube connecting pipe (12) communicated with the stomach decompression tube (2) and a mask body breather tube (13) communicated with the mask body cavity (19), the stomach decompression tube connecting pipe (12) and the mask body breather tube (13) are isolated from each other, and an embedded positioning port (18) communicated with the stomach decompression tube connecting pipe (12) is arranged at an end, away from the mask body bottom plate (1), of the mask body tube (3).

* * * * *